(12) United States Patent
Wingo et al.

(10) Patent No.: US 7,841,226 B1
(45) Date of Patent: Nov. 30, 2010

(54) PROBOSCIS EXTENSION REFLEX PLATFORM FOR VOLATILES AND SEMI-VOLATILES DETECTION

(75) Inventors: Robert M. Wingo, Los Alamos, NM (US); Kirsten J. McCabe, Los Alamos, NM (US); Timothy K. Haarmann, Jemez Pueblo, NM (US)

(73) Assignee: U.S. Department of Energy, Washington, DC (US)

( * ) Notice: Subject to any disclaimer, the term of this patent is extended or adjusted under 35 U.S.C. 154(b) by 450 days.

(21) Appl. No.: 12/039,770

(22) Filed: Feb. 29, 2008

Related U.S. Application Data

(60) Provisional application No. 60/975,948, filed on Sep. 28, 2007.

(51) Int. Cl.
*G01N 9/00* (2006.01)
(52) U.S. Cl. .................................................... 73/31.05
(58) Field of Classification Search ................. 73/31.05
See application file for complete search history.

(56) References Cited

U.S. PATENT DOCUMENTS

| H145 H | * | 10/1986 | James | ........................ 600/529 |
| 7,237,504 B2 | * | 7/2007 | Davis et al. | ................... 119/6.5 |

* cited by examiner

*Primary Examiner*—John Fitzgerald
*Assistant Examiner*—Alex Devito
(74) *Attorney, Agent, or Firm*—Thomas S. O'Dwyer; James C. Durkis

(57) ABSTRACT

The present invention provides an apparatus for the detection of volatile and semi-volatile chemicals using the olfactory abilities of honey bees that are trained to respond to the presence of a specific chemical in a sample of gas with the proboscis extension reflex (PER). In particular, the geometry and arrangement of the parts of the apparatus are such that the amount of surface area in contact with the sample of gas prior to its introduction to the bees is minimized to improve the detection of particular volatile and semi-volatile that have a tendency to "stick" to contacting surfaces, especially certain chemicals associated with explosives and narcotics. According to another aspect of the present invention, a pre-concentrating means is incorporated with the device to effectively increase the concentration of "sticky" chemicals presented to the insects.

20 Claims, 8 Drawing Sheets

PROBOSCIS EXTENSION REFLEX PLATFORM FOR VOLATILES AND SEMI-VOLATILES DETECTION

CROSS-REFERENCE TO RELATED APPLICATIONS

This application claims the benefit of the earlier filing date of Provisional Application No. 60/975,948 filed on Sep. 28, 2007.

GOVERNMENT INTEREST STATEMENT

The United States Government has rights in this invention pursuant to LANS Contract No. DE-AC52-06NA25396 between the United States Department National Nuclear Security Administration and Los Alamos National Security, LLC for the operation of Los Alamos National Laboratory.

BACKGROUND

1. Field of the Invention

The present invention relates generally to the detection of volatile and semi-volatile materials, and more particularly, to the use of insects to assist in the detection of volatile and semi-volatile materials, especially "sticky" volatile and semi-volatile chemicals that have a tendency to adhere to contacting surfaces, are present in low concentrations, and are commonly associated with certain types of explosives and narcotics.

2. Related Art

Volatile and semi-volatile chemicals may be detected in the field with portable instruments or in the laboratory with previously collected samples. Typically, these instruments use chromatographic separation (e.g., gas chromatography) to detect the volatile or semi-volatile chemical, but in some cases, these instruments may use ion mobility spectrometry.

There are also non-instrumental techniques available for the detection of volatile or semi-volatile chemicals. For example, indicator papers that change color are available for the detection of some analytes. However, the number of analytes detectable by this approach is very limited. Most non-instrumental detection methods are dominated by the use of trained mammalian systems (e.g., canines) that use their olfactory ability to report detection of a volatile or semi-volatile chemical. Canines have been used extensively for smuggling interdiction, explosives detection, search and rescue, etc.

As an alternative, the olfactory abilities of insects can be harnessed for use in detecting the presence of volatile or semi-volatile chemicals. This can be achieved by monitoring or observing an instinctual or trained behavior exhibited by the insect in response to sensing the presence of the volatile or semi-volatile chemical. In particular, honey bees, *Apis mellifera*, can be utilized for vapor detection of such chemicals by monitoring their Proboscis Extension Reflex (PER). Neurologists, psychologists, physiologists and others have utilized PER in bees as a model for examining learning and memory. Studies have shown that bees can be trained or conditioned to exhibit PER in response to sensing a specific volatile and semi-volatile chemical. (See, e.g., Abramson et al., Learning in the Africanized Honey Bee: *Apis Mellifera* L. *Phys. & Behavior* 62: p. 657-74 (1997); See also Bitterman et al., Classical Conditioning of Proboscis Extension in Honeybees *Journal of Comp. Psychology* 97: 107-19 (1983), the contents of both are hereby incorporated by reference).

In contrast to their mammalian counterparts, honey bees are much less expensive to raise, train and deploy, as well as being self renewing, relative to canines. A "handler" is not necessary for each and every honey bee. A trainer may be centrally located and capable of producing and deploying hundreds of sensors/conditioned honey bees daily.

Furthermore, observation of the trained PER behavior displayed by the insect in response to a specific vapor or odor can be facilitated by using instrumentation capable of monitoring such behavioral movements of the bees and recording, displaying, or communicating a positive test event to the user. Portable instruments that use insects to detect the presence of volatile or semi-volatile compounds have been developed. For instance, a patent issued to Davis et al. (U.S. Pat. No. 7,237,504, the contents of which are hereby incorporated by reference) describes a portable device that uses a camera to detect the PER response of bees in response to a volatile chemical of interest.

Commercial applications that use the olfactory abilities of honey bees vary widely and include transportation security, search and rescue, narcotics interdiction, medical diagnostics, food quality/control, facility security, and any other industry that would benefit from having the capability to qualitatively detect whether a volatile or semi-volatile is present in a product or item.

However, several problems and limitations exist with the current state of the art for apparatuses capable of harnessing the olfactory abilities of insects. For instance, one critical limitation with existing prototypes and products is that they are not designed to achieve detection of volatile chemicals at very low concentrations. This is especially important and challenging for certain types of "sticky" volatile and semi-volatile chemical vapors that are emitted from explosives and some types of narcotics since they tend to adhere to contacting surfaces, thus lowering their effective concentration in a sample of air even further (typically at low ppt). (See, e.g., Gowadia, H. A. and Settles, G. S., The natural sampling of airborne trace signals from explosives concealed upon the human body. *Journal of Forensic Sciences* 46(6), (2001), the contents of which are hereby incorporated by reference.)

The Davis patent (U.S. Pat. No. 7,237,504) as well as existing prototypes and products for bee sensing apparatuses all utilize extensive ducting means that comprise tubes, valves, and branches to deliver individual streams of air to each individual insect. This arrangement greatly increases the amount of surface area within the instrument that comes in contact with the air sample to be tested prior to presentation to the insects for detection. As a result, the ability of these existing devices to detect "sticky" volatile and semi-volatile chemicals present in a sample at low concentrations is limited.

Therefore, a need exists in the art for an improved portable device or apparatus that is capable of harnessing the sensing abilities of insects in a way that allows detection of volatile and semi-volatile chemicals present in a sample at low concentrations and that overcomes the tendency of some of these vapors to stick to contacting surfaces.

SUMMARY

The Los Alamos National Laboratory (LANL) has developed a Proboscis Extension Reflex Platform (LANL-PERP) that allows for conditioned honey bees to be used as detectors for volatile and semi-volatile chemicals that does not require direct visual interpretation of the PER response.

The LANL-PERP concept comprises a housing into which restrained and conditioned/trained insects or honey bees are placed. The instrument incorporates hardware for the delivery of volatiles and semi-volatiles to trained honey bees, detection of the vapors by monitoring for PER behavior by the bees, and electronics/software for producing an unambiguous output/electronic response when PER is detected.

Honey bees used with LANL-PERP are trained to detect volatile and semi-volatile chemicals or analytes of interest present in a sample of gas via associative learning. Exposure to the chemical or analyte of interest, followed by a sugar solution reward, trains the bees to stick out their proboscis (tongue) in anticipation of receiving the reward when exposed to the chemical or analyte of interest. This behavior is referred to as the proboscis extension reflex (PER) and is capable of being monitored by a computer utilizing a camera to observe the PER behavior of the bees and communicate, display, or record a positive event for detection to the user. The LANL-PERP device may utilize either pattern recognition software or simple changes in light intensity. Alternatively, PER recognition may be carried out visually by a user or operator of the LANL-PERP by observing a screen.

The present invention seeks to improve the detection of "sticky" volatile and semi-volatile chemicals present in a sample at low concentrations through a variety of approaches. One aspect of the present invention is designed to overcome the difficulty of detecting "sticky" volatile and semi-volatile chemicals present in a sample of gas at low concentrations by decreasing the surface area that comes in contact with the air sample prior to its exposure to the bees for detection. This is accomplished through changes in the overall geometry of the device by incorporating the following features: First, the bees are moved closer to the inlet where the air sample enters the device, thus limiting the distance that the air must travel before reaching the bees. Second, extensive ductwork comprising tubes, valves, and branches as used by prior art devices to deliver individual streams of air to the bees is eliminated. Instead, the air sample enters the device through a common channel or slit approximately the width of the arrangement of bees in the chamber.

Therefore, by decreasing the distance for the sample of gas or air to travel and by eliminating any ducting means (including tubes, valves and/or branches) to deliver the sample to each of the bees, the surface area within the device that comes in contact with the air sample prior to its exposure to the bees is substantially decreased. As a result, the amount of absorptive loss is reduced, and the detection of "sticky" volatile or semi-volatile chemicals present in a sample of gas at low concentrations is improved.

Another aspect of the present invention seeks to take advantage of the properties of these "sticky" volatile and semi-volatile chemicals to work toward increasing their detection. A pre-concentrating means is optionally attached to the front end of the device directly in front of the inlet of the channel that leads to the bees. The pre-concentrator comprises a metal strip or mesh that is placed in front of the opening of the inlet. After passing an air sample over the metal strip or mesh for a period of time, any such "sticky" chemical compounds that are present in the sample are allowed to adhere to the metal strip or mesh. Subsequently, the "sticky" chemical compounds adhered to the metal strip or mesh can be released in a single pulse at a higher concentration by resistively heating the metal over a short period of time. This improves the probability of detecting such "sticky" chemicals present in the air sample by using the properties of such chemicals to generate a more concentrated pulse for testing. In other words, the pre-concentrator increases the vapor-phase concentration of the analyte in the gas sample presented to the bees during the pulse.

Another aspect of the present invention is to use a smaller fan that decreases the velocity of the air passing over the bees. By using lower air speeds (for example, 0.05-0.3 m/s), detection should be increased by more closely mimicking the natural flight speeds of honey bees while they are foraging and transiting between flowers.

Yet another aspect of the present invention is to increase the number of detectors or bees that are used per device. Statistically, to create a device that minimizes the number of false positive and negative events, it is important to increase the number of detectors or bees to provide greater assurance and reliability of each test. Further, by increasing the number of detectors or bees per unit device, there exists the possibility of using some of the bees to perform a control function, thus helping to eliminate any background effects that might lead to false detection.

BRIEF DESCRIPTION OF THE DRAWINGS

The invention will be described in conjunction with the accompanying drawings, in which.

DETAILED DESCRIPTION OF THE PREFERRED EMBODIMENTS

Definitions

It is advantageous to define several terms before describing the invention. It should be appreciated that the following definitions are used throughout this application.

The term "insect" includes any insect that is capable of displaying a consistent behavior in response to sensing a specific volatile or semi-volatile chemical. The term "insect" includes an insect that is trained or conditioned to display an observable behavior. The term "insect" includes an insect that displays the proboscis extension reflex (PER). The term "insect" includes a honey bee.

The terms "sticky" or "stickiness" refer to volatile or semi-volatile chemicals that have a tendency to adhere and collect on contacting surfaces or substrates.

Description

Figure 1:
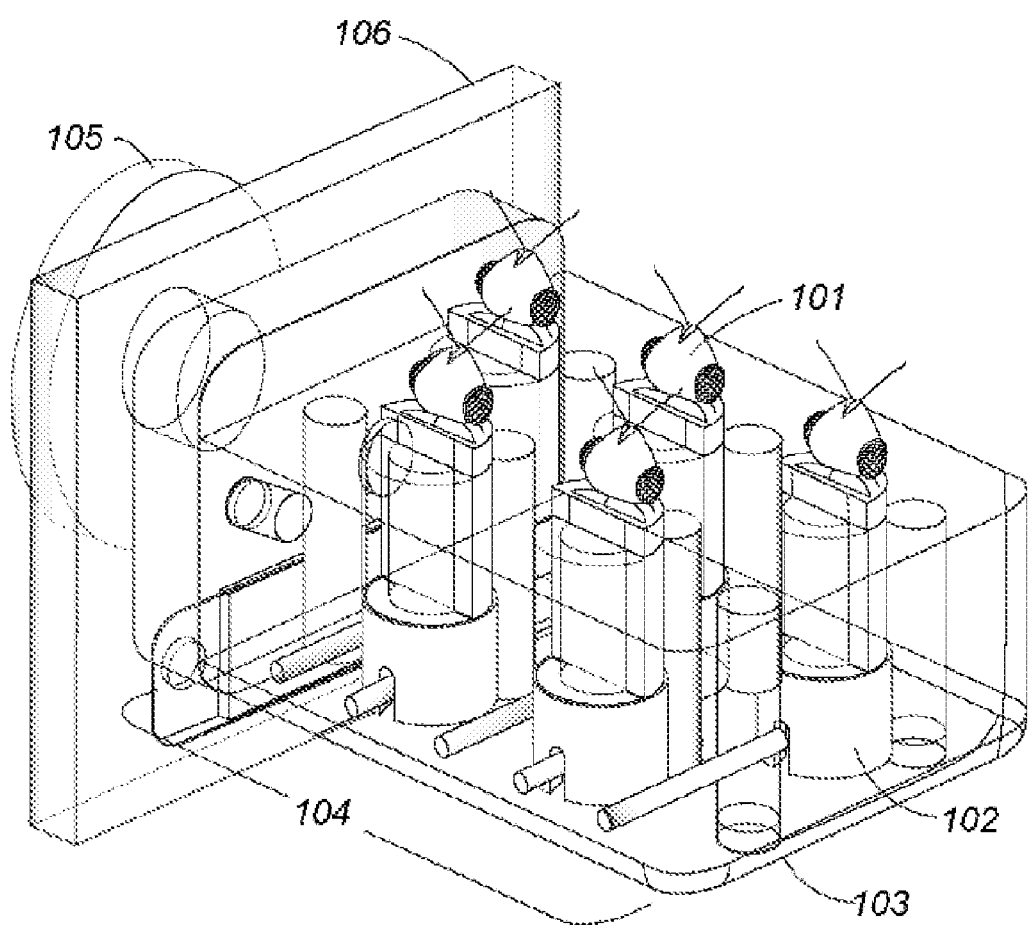
FIG. 1 is a side view of the bee holding unit showing the individual yokes containing the bees fixed to the base of the holding tray and the outer surface of the holding tray that optionally includes a latch and knob.

As shown in FIG. 1, two or more insects or bees 101 (preferably five or more bees) are placed and constrained in individual yokes 102 arranged in parallel such that the head of each bee is visible from at least one single vantage point within the instrument to allow for simultaneous observation of a PER event. The yokes are fixed in a predetermined and patterned arrangement onto the base 103 of the holding tray 104 such that the fixed end of each yoke corresponds to the posterior end of each bee with the anterior (head) end of the bee pointed in the opposite direction away from the base of the holding tray. Further, the heads of each bee are arranged such that they are substantially co-planar with each other and such that no other bee is placed either directly in front of or directly behind of another bee within the axis of air flow so that each bee receives its own portion of the air flow. However, it is not required that the bees are arranged linearly and are preferably arranged according to one embodiment in a non-linear array. The holding tray 104 is capable of being removably inserted into the device, and handling of the holding tray may be facilitated by the use of a knob 105 fixed to the outer surface 106 of the holding tray to become substantially flush with the outer casing (not shown) of the device when fully inserted.

According to one aspect of the invention, five or more bees 101 are used to detect the presence of a volatile or semi-volatile chemical. Using an increased number of bee detectors (i.e., bees) allows for a statistically more accurate detection by reducing the number of false positives or negatives that might occur as a result of one or more errant bees. Increasing the number of bees also allows for the additional implementation of control (e.g., untrained) bees to make positive test events more reliable by helping to eliminate background effects that might contribute to a false event.

Figure 2A:
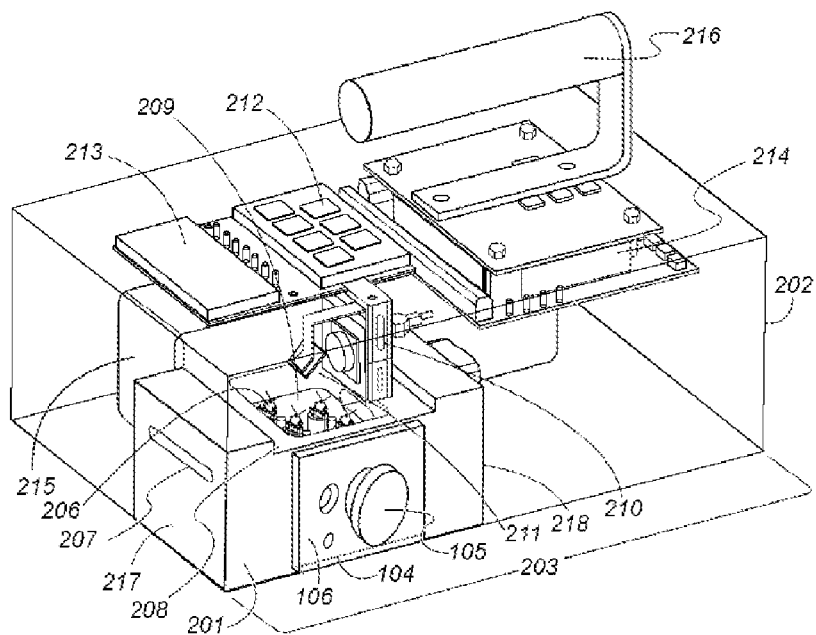
FIG. 2A is a view of one embodiment of the invention from the front and right corner of the device assembly.
Figure 2B:
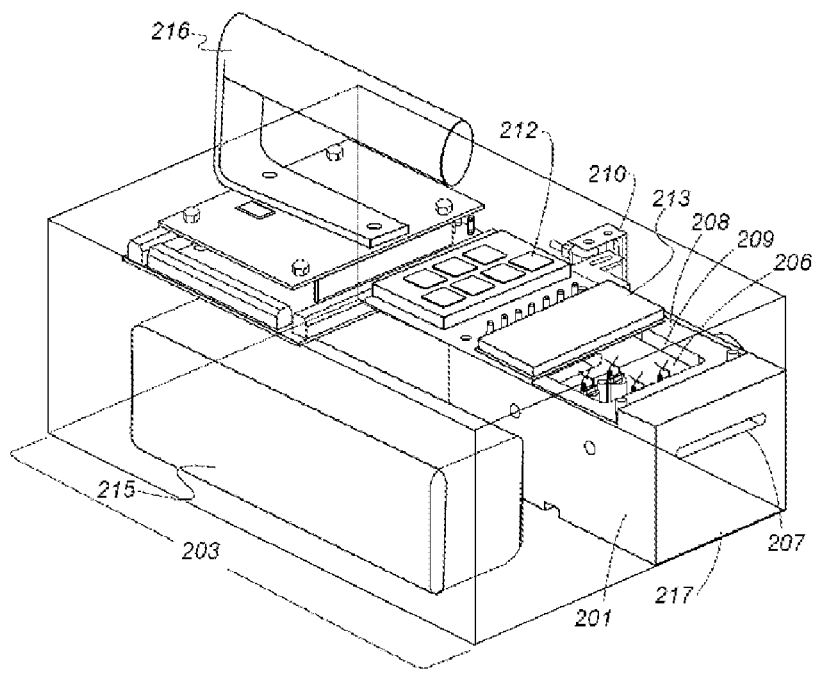
FIG. 2B is a view of the same embodiment of the invention from the front and left corner of the device assembly.

FIG. 2A and FIG. 2B show one embodiment of the invention. The holding tray 104 is fully inserted into the housing 201 using the knob 105 attached to the outer surface 106 of the holding tray until the outer surface of the holding tray is substantially flush with the outer surface of the housing 201 and outer casing 202 of the device assembly 203. Once inserted, the bees are positioned inside the chamber 206 of the housing 201. A latch or similar mechanism (not shown) may be attached to the inner surface of the holding tray 104 to allow the holding tray to remain stably fixed in place once it is fully inserted. The inlet 207 of the housing 201 is placed on the front portion 217 of the housing and is oriented to face outward and to be substantially flush with outer casing 202 of the device assembly 203 to allow for the air sample to enter the device from outside the device. The flow of air is generated by a fan (not shown) preferably positioned on the rear portion 218 of the housing 201 that is opposite the inlet 207 to generate a negative pressure that pulls the air through the device.

In further reference to FIG. 2A and FIG. 2B, the upper portion 208 of the chamber of the housing creates an opening 209 to allow the PER behavior of the bees to be observed. In an alternative embodiment, the opening 209 on the upper portion 208 of the chamber is covered with a transparent material. The present invention further includes a means for monitoring the insects. According to one embodiment, the monitoring means is preferably a camera 210 that is fixed to the upper portion 208 of the housing 201 such that the camera faces away from the position of the bees and uses a mirror 211 that is angled to put the bees in view of the camera. A light source (not shown) is also included in the chamber of the housing to allow the monitoring means to visualize the bees. Preferably, the light source is placed near the base 103 of the holding tray 104 to provide a backlight for viewing the bees. The present invention further includes a means for focusing the camera preferably on the heads of the bees.

The present invention includes a means for inputting commands to the device, which preferably comprises a keypad 212. The present invention also includes an outputting means or readout 213 for displaying the results of a test. The keypad and readout are positioned so that they are substantially flush with the outer surface of the device casing 202 to allow the user to access the keypad and observe the readout. The present invention further includes a computer means 214 for processing the visual data to determine if a positive PER event has occurred and directing the outputting means to communicate or display the results of a test in the appropriate format. Finally, the present invention uses either a battery 215 or other power source to provide the necessary electricity to power the system, including namely the fan 303, the optional pre-concentrating means 401, the outputting 213 and inputting 212 means, the light source 304, and the computer means 214. Finally, a carrying handle 216 is optionally included to allow the user to carry the instrument in a facilitated manner.

Figure 3:
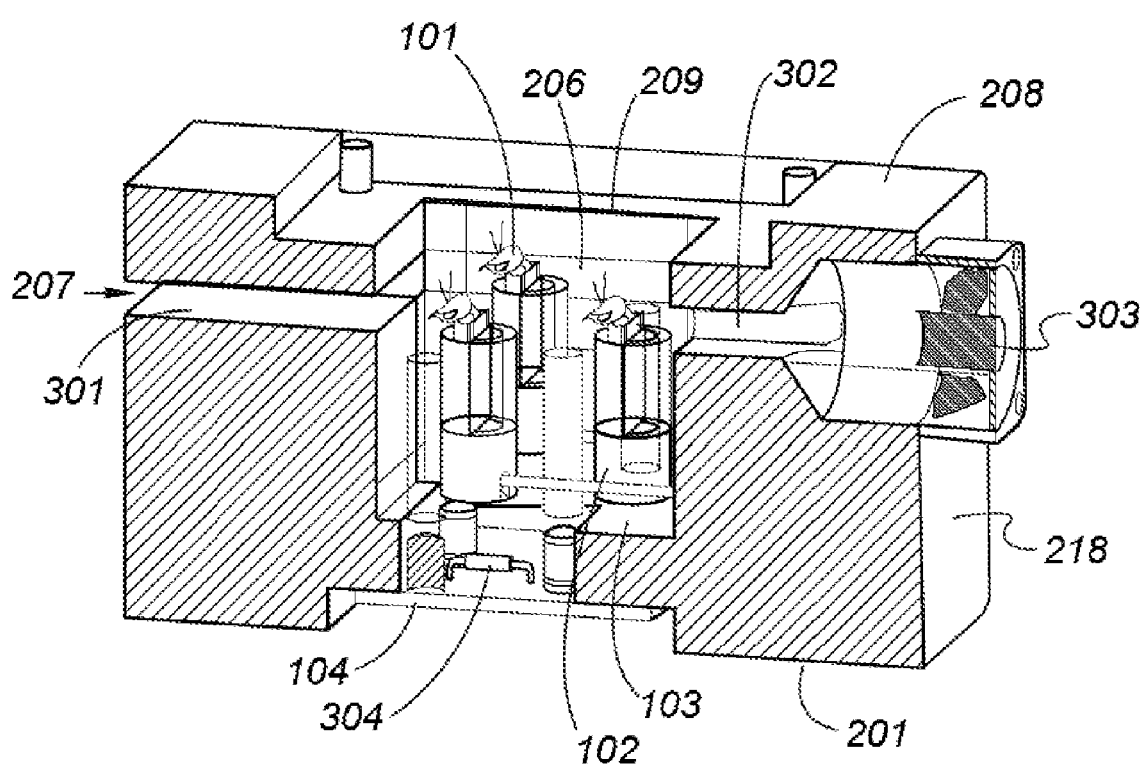
FIG. 3 is a cross-sectional view of the housing showing the position of the bees relative to the plane of air flow.

FIG. 3 provides a cross-sectional view of a preferred embodiment for the housing 201. The air is first pulled into an inlet 207 on the front portion 217 of the housing and travels through a first channel 301 of the housing toward the chamber 206 where the bees are located. Said first channel is approximately the width of the arrangement of bees in the chamber and is approximately co-planar with the arrangement of the heads of the bees. Importantly, said first channel does not divide the air flowing to each bee detector but is instead substantially arranged as a horizontal slot, thus avoiding any unnecessary increase in surface area for the channel. In other words, said first channel creates one flow of air that is common to all of the bees. In addition, said first channel 301 is relatively short in length, thus placing the bees 101 closer to the inlet 207 and further reducing the surface area in contact with the air sample prior to exposure to the bees.

The air sample is pulled into the housing 201 by a fan 303 that is preferably placed on the rear portion 218 of the housing generating an air flow that is substantially unidirectional and planar. Thus, the air flow through the housing is substantially as follows: First, the air enters the inlet 207 on the front portion 217 of the housing. Second, the air travels through a common first channel 301 that is relatively short. Next, the air enters the chamber 206 in a substantially planar flow around the heads of the bees 101. Finally, the air exits the chamber and flows out of the housing through a second channel 302 and a fan 303 mounted on the rear portion 218 of the housing that pulls the air through it.

The cross sectional view of the housing in FIG. 3 further displays the preferred location for the light source 304 near the base 103 of the holding tray 104 to provide backlighting for the camera. The cross sectional view further shows the opening 209 on the upper portion 208 of the housing 201 that allows for the PER behavior of the bees to be observed by the monitoring means or camera. In an alternative embodiment, the opening 209 on the upper portion 208 of the housing is covered by a transparent material.

Figure 4:
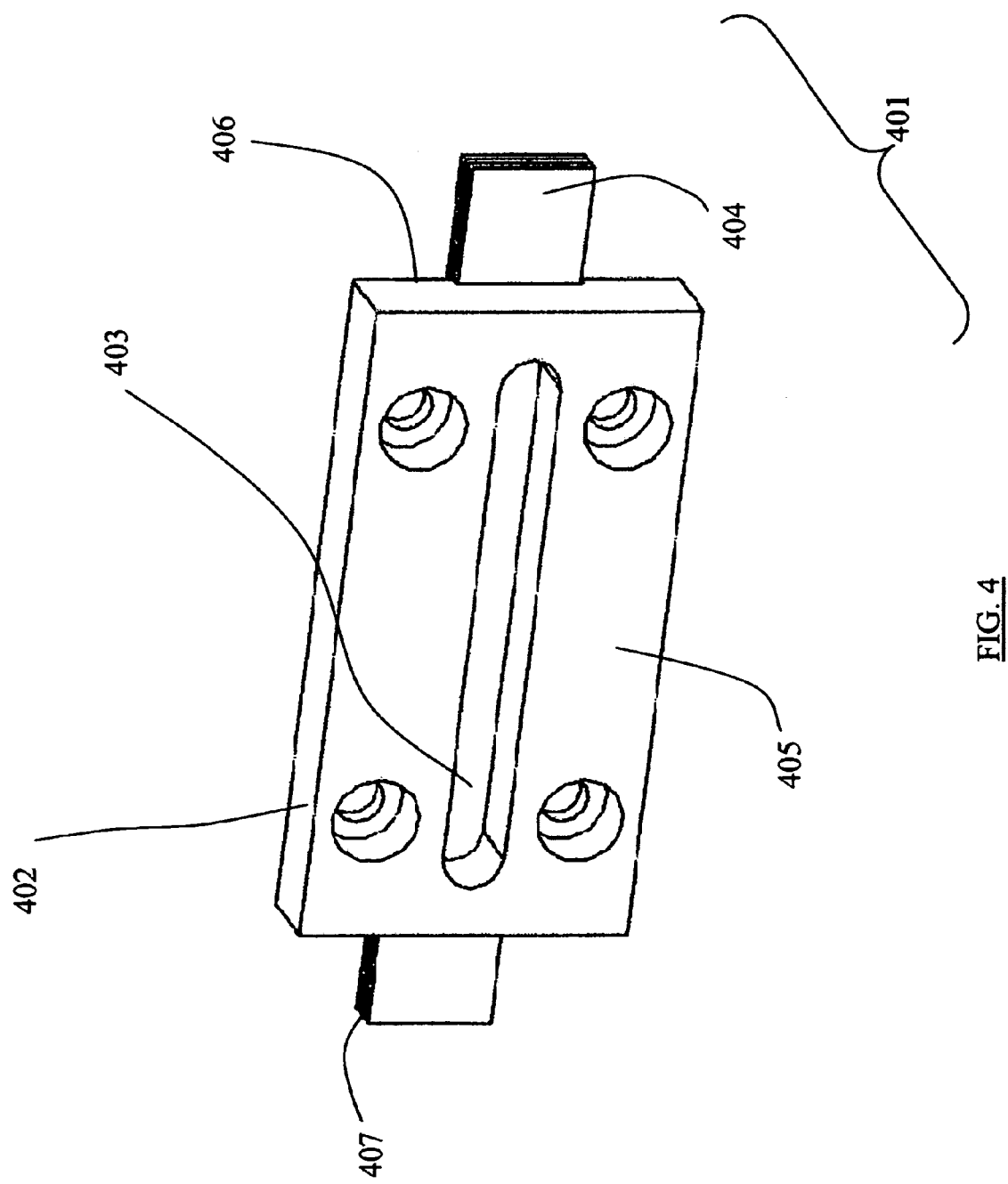
FIG. 4 is a front view of the pre-concentrator assembly.

As depicted in FIG. 4, the present invention may optionally include a pre-concentrator assembly 401. When engaged, the pre-concentrator includes a holder 402 that is mounted with the front surface 405 of said holder placed in front of the inlet 201 on the front portion of the housing 601. Said holder has a horizontal slot 403 of nearly identical size and dimension as said inlet 201 and said first channel 301. The slot of said holder is attached to the housing such that said slot of the holder is placed directly in front of and is fully continuous with said inlet and said first channel. A metal strip or mesh 404 is removably placed over the rear surface 406 of the holder in contact with the entire opening of the slot and a portion of the holder. An insulating spacer 407 is placed between said metal strip or mesh 404 and said portion of the holder covered by said metal strip or mesh such that the spacer does not block any portion of the slot 403 or inlet 201 of said first channel to allow unimpeded air flow into the device. A sandwich assembly may thereby be formed by placing pieces 404 and 407 in alternating layers. Further, the metal strip or mesh 404 is attached to an electrical source (not shown), and in one preferred embodiment, the metal strip or mesh 404 is composed of stainless steel.

To operate the pre-concentrator, the air sample is passed over the metal strip or mesh 404 over a period of time to allow "sticky" volatile or semi-volatile compounds to adhere to said metal strip or mesh. Once a sufficient or predetermined volume of air sample has been passed over the metal strip or mesh, said metal strip or mesh is attached to the pre-concentrator as described above (if not already attached), and a pulse of electrical current is introduced by an attached power source (not shown) to the metal strip or mesh at a predetermined level. The current introduced to said metal strip or mesh produces resistive heating I the metal that causes any "sticky" volatile or semi-volatile compounds that may have adhered to said metal strip or mesh to be released over a short period of time, thus increasing the concentration of the volatile or semi-volatile compounds presented to the bees during the pulse (compared to concentrations present in the air) to improve the probability that the bees will be able to detect and report the presence of sticky compounds that are present in the air sample at low concentrations.

Figure 5:
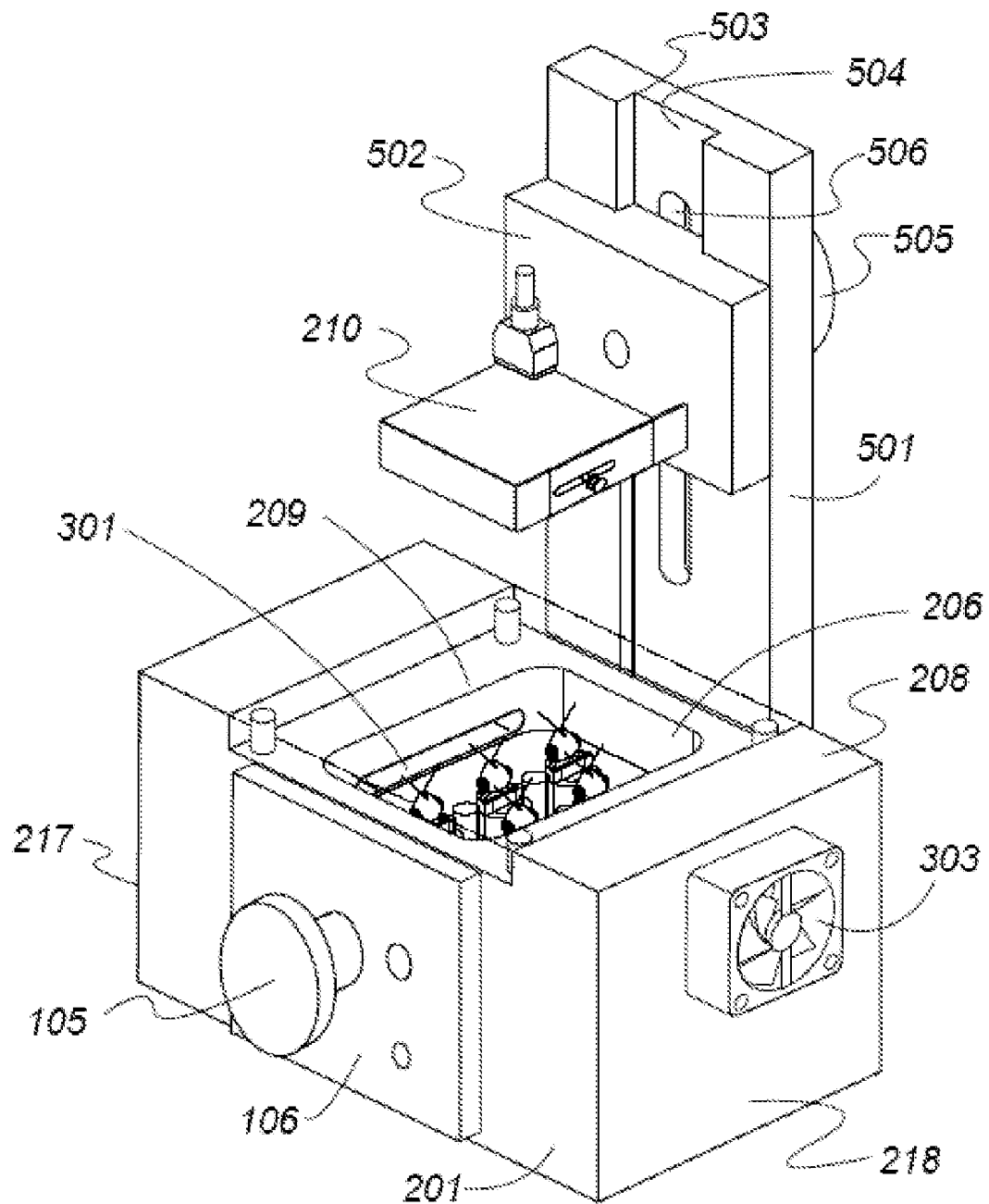
FIG. 5 is a view of one embodiment of the present invention having the camera in an alternative position compared to the embodiment shown in FIG. 2.

FIG. 5 presents an alternative arrangement for the placement of the monitoring means or camera. Although the arrangement of the housing, holding tray, etc. are identical in this alternative embodiment as described above, the camera 210 is placed directly above and in direct view of the bees. The camera is mounted onto a plate 502 that is designed to slide on the upper portion of a mounting bracket 501 with the bracket stem mounted on its lower portion to the housing. Movement of the plate is along the major axis of the bracket 501 and is restricted by a tongue-in-groove mechanism that utilizes a projection 503 of the plate that tightly fits inside an indentation 504 of the bracket, thus allowing the camera and plate to slide only along a the major axis of the bracket (i.e., toward and away from the bees). The adjustable movement of the plate and camera allows for the camera to focus on the plane of the heads of the bees.

Figure 6A:
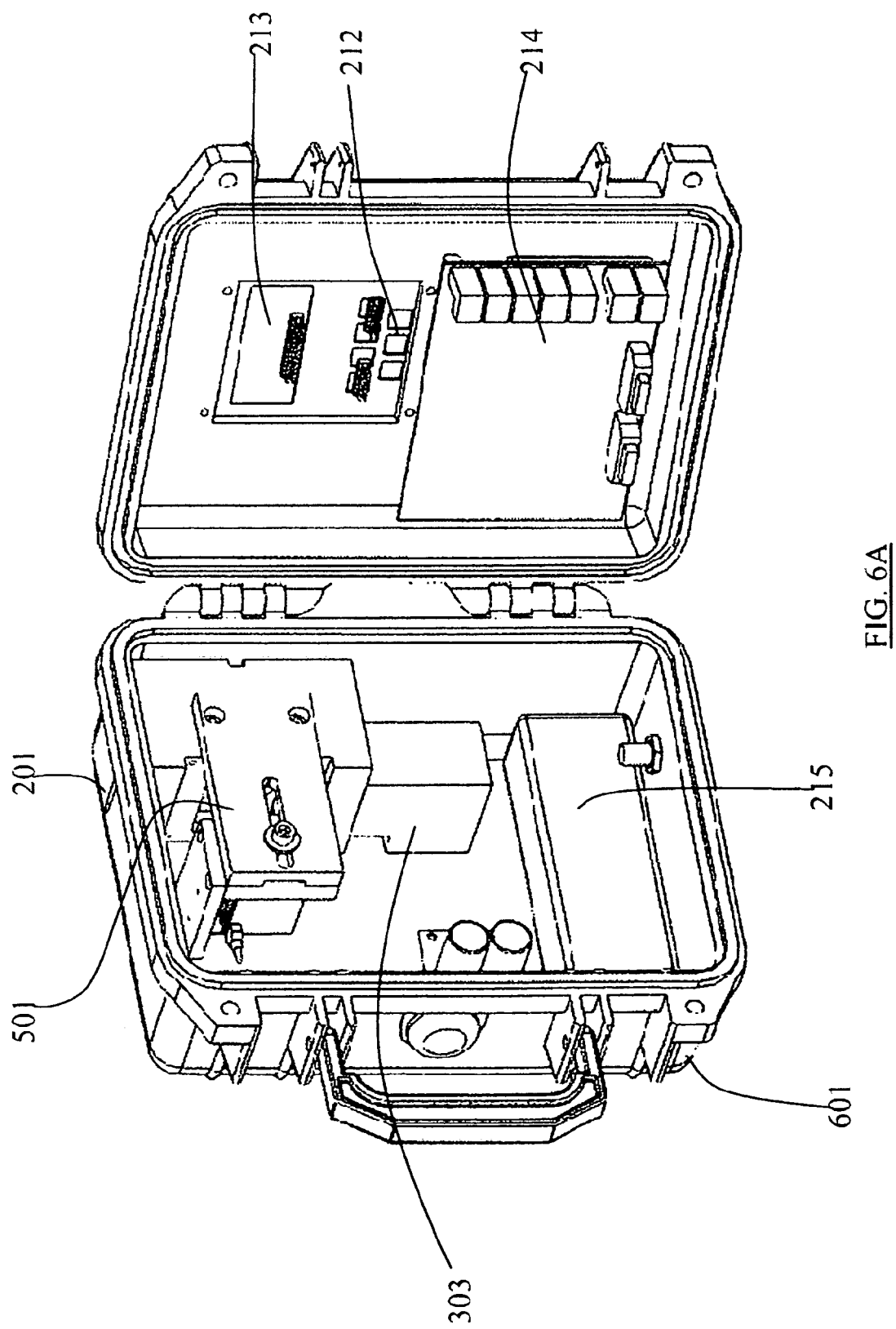
FIG. 6A shows an interior view of an alternative arrangement for the present invention with the camera in the different orientation as shown in FIG. 5.
Figure 6B:
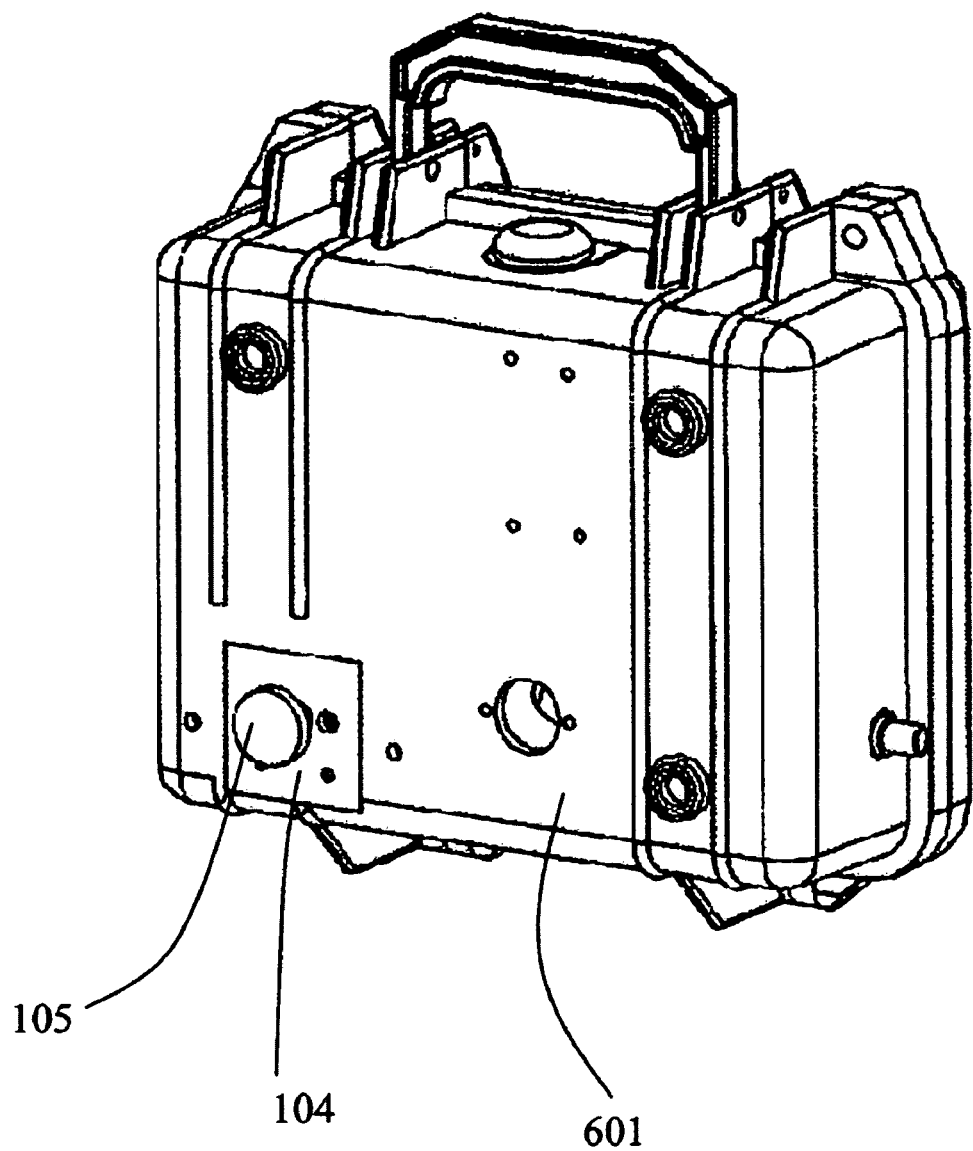
FIG. 6B and FIG. 6C show opposing outer views of the alternative assembly shown in FIG. 6A.
Figure 6C:
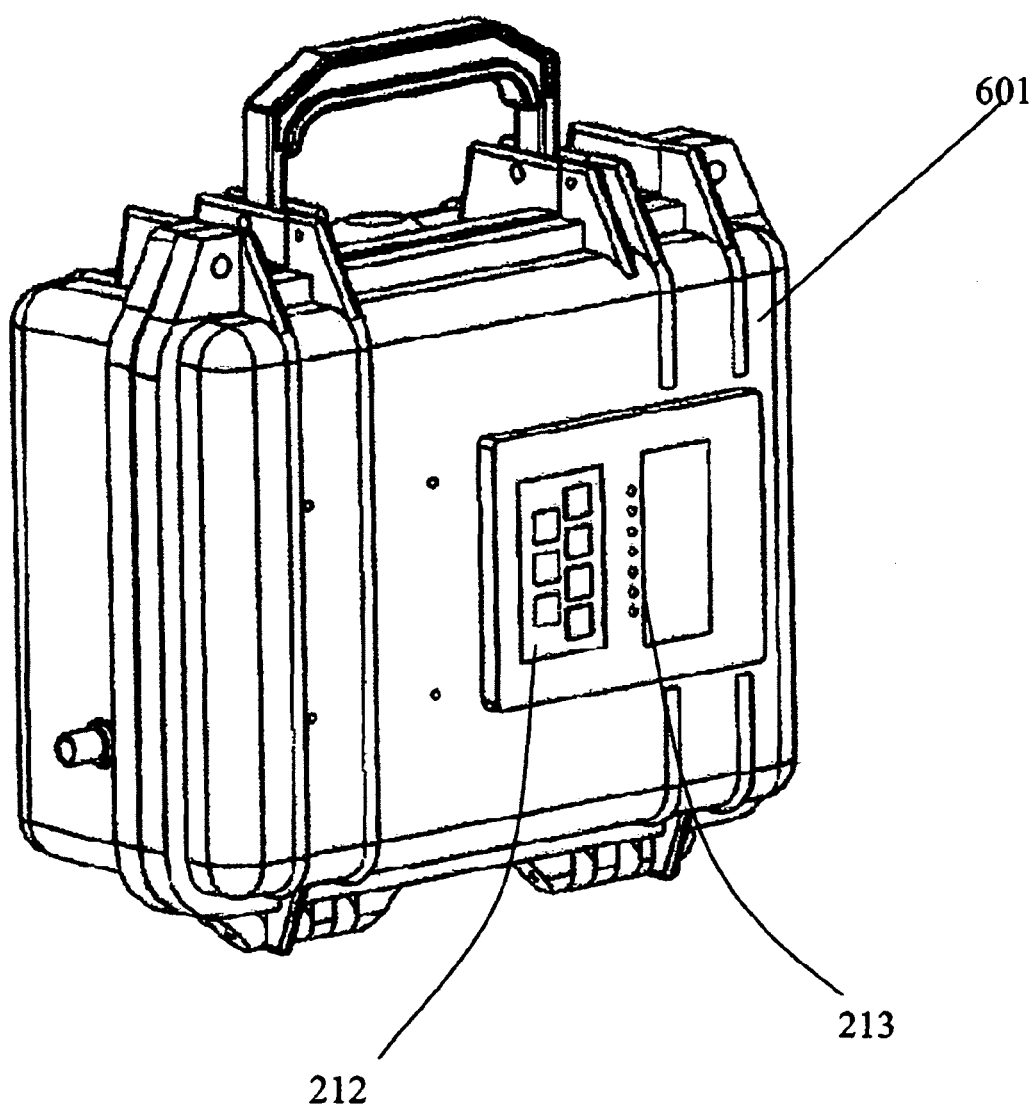

When the height of the camera and plate are at the appropriate height such that a focused image of the heads of the bees is created, the position of the camera and plate along the major axis of the bracket can be fixed in place by tightening a screw knob 505. Said screw knob has a screw portion (not shown) that goes through an opening 506 of the bracket with said opening oriented lengthwise along the major axis of said mounting bracket 501 preferably within said indentation 504 of the bracket. Said screw portion of said screw knob also screws into the plate 502 on the opposite surface of the camera. This screw knob mechanism allows for the plate and camera to be fixed at a desired height along the major axis of the bracket when the screw knob is tightened. As shown in FIGS. 6A, 6B, and 6C, the alternative arrangement in FIG. 5 showing placement of the camera directly above the bees may be incorporated into an alternative type of device. All of the major components of the present invention are also provided in this alternative embodiment and function identically as described above, even though the relative placement of the holding tray 104, keypad 212, readout 213 in this alternative embodiment are repositioned.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

Davis et al., "Detection of Odors Using Insects," (U.S. Pat. No. 7,237,504) Issued Jul. 3, 2007.

Bitterman, M. E., "Classical Conditioning of Proboscis Extension in Honeybees (*Apis Mellifera*)," *Journal of Comparative Psychology*, 97 (2), p. 107-119 (1983).

Guirfa, M., "Associative Mechanosensory Conditioning of the Proboscis Extension Reflex in Honeybees", *Learning and Memory*, 11, p. 294-302 (2004).

Sandoz, J. C. et. al., "Asymmetrical generalisation between pheromonal and floral odours In appetititive olfactory conditioning of the honey bee (*Apis mellifera* L.)", *Journal of Comparative Physiology A*, 187, p. 559-568 (2001).

Ray, S., Ferneyhough, B., "Behavioral Development and Olfactory Learning in the Honeybee (*Apis Mellifera*)" John Wiley and Sons, Inc. (1999).

Pelz, C. et. al., "Odorant intensity as a determinant for olfactory conditioning in honeybees: roles in discrimination, overshadowing and memory consolidation", *The Journal of Experimental Biology* 200, p. 837-847 (1997).

Abramson, C. I., et. al., "Learning in the Africanized Honey Bee: *Apis mellifera* L." *Physiology and Behavior*, 62 (3), p. 657-674 (1997).

Friedrich, A., Thomas, U., Muller, U., "Learning at Different Satiation Levels Reveals Parallel Functions for the cAMP-Protein Kinase A Cascade in Formation of Long-Term Memory", *The Journal of Neuroscience*, p. 4460-4468 (2004).

What is claimed is:

1. An apparatus for detecting the presence of a volatile or semi-volatile chemical in a sample of gas during a test using insects, the apparatus comprising:

a holding tray, comprising a yoke for each insect, wherein at least two insects are restrained in said yokes and wherein said yokes are fixed to a base of said holding tray in a predetermined arrangement;

a housing, having a means for removably inserting said holding tray into a chamber of said housing and having a means for causing movement of said sample of gas through the housing in a predetermined direction, wherein said housing has a first channel and a second channel with said first channel placed upstream of the chamber and said second channel placed downstream of the chamber relative to the direction of movement of said sample of gas, wherein a width of said first channel and said second channel is approximately the width of said predetermined arrangement of the insects in said chamber, and wherein the flow of said sample of gas is common to each of the insects due to said first channel being undivided;

means for monitoring the insects, to observe a specific behavior by the insects in response to the insect detecting the presence of the volatile or semi-volatile chemical in said sample of gas;

means for outputting the detection of the volatile or semi-volatile chemical in a sample of gas by the insects; and a power source.

2. The apparatus of claim 1, wherein said outputting means displays, records, or communicates the result of a test.

3. The apparatus of claim 1, wherein said first channel of the housing does not contain any additional tubes, valves, or branches.

4. The apparatus of claim 1, wherein said predetermined arrangement of the insects is such that the head of each insect is substantially co-planar and simultaneously visible from a single viewpoint.

5. The apparatus of claim 1, wherein at least five insects are restrained said yokes of said holding tray.

6. The apparatus of claim 1, wherein said means for causing movement of the sample of gas is a fan.

7. The apparatus of claim 1, wherein said sample of gas is air.

8. The apparatus of claim 1, wherein said means for monitoring the insects is a camera.

9. The apparatus of claim 1, wherein said power source is a battery.

10. An apparatus for detecting the presence of a volatile or semi-volatile chemical in a sample of gas during a test using insects, the apparatus comprising:
    a holding tray, comprising a yoke for each insect, wherein at least two insects are restrained in said yokes and wherein said yokes are fixed to a base of said holding tray in a predetermined arrangement;
    a housing, having a means for removably inserting said holding tray into a chamber of said housing and having a means for causing movement of said sample of gas through said housing in a predetermined direction, wherein said housing has a first channel and a second channel with said first channel placed upstream of the chamber and said second channel placed downstream of the chamber relative to the direction of movement of said sample of gas, wherein said means for causing movement of said sample of gas is a fan, and wherein said fan causes said sample of gas to flow at a rate of between 0.05 and 0.30 m/s;
    means for monitoring the insects, to observe a specific behavior by the insects in response to the insect detecting the presence of the volatile or semi-volatile chemical in said sample of gas;
    means for outputting the detection of the volatile or semi-volatile chemical in a sample of gas by the insects; and
    a power source.

11. The apparatus of claim 10, wherein said flow rate of the sample of gas is approximately 0.10 m/s.

12. The apparatus of claim 10, wherein said flow rate of the sample of gas is adjustable.

13. The apparatus of claim 10, wherein a width of said first channel and said second channel is approximately the width of said predetermined arrangement of the insects in said chamber and wherein the flow of said sample of gas is common to each of the insects due to the first channel being undivided.

14. The apparatus of claim 10, wherein at least five insects are restrained said yokes of said holding tray.

15. The apparatus of claim 10, wherein said sample of gas is air.

16. The apparatus of claim 10, wherein said means for monitoring the insects is a camera.

17. The apparatus of claim 10, wherein said power source is a battery.

18. An apparatus for detecting the presence of a volatile or semi-volatile chemical in a sample of gas during a test using insects, the apparatus comprising:
    a holding tray, comprising a yoke for each insect, wherein at least two insects are restrained in said yokes and wherein said yokes are fixed to a base of said holding tray in a predetermined arrangement;
    a housing, having a means for removably inserting said holding tray into a chamber of said housing and having a means for causing movement of said sample of gas through said housing in a predetermined direction, wherein said housing has a first channel and a second channel with said first channel placed upstream of said chamber and said second channel placed downstream of said chamber relative to the direction of movement of said sample of gas, and wherein said first channel has an inlet where the sample of gas enters said first channel from the exterior of the apparatus;
    means for pre-concentrating the volatile or semi-volatile chemical, said pre-concentrating means comprising a metal strip or mesh attached to a holder that is placed in front of the inlet of said first channel that is capable of collecting a volatile or semi-volatile chemical on its surface due to the properties of the volatile or semi-volatile chemical and releasing the volatile or semi-volatile chemical in a controlled manner by introducing a pulse of electric current to the metal strip or mesh;
    means for monitoring the insects, to observe a specific behavior by the insects in response to the insects detecting the presence of the volatile or semi-volatile chemical in said sample of gas;
    means for outputting the detection of the volatile or semi-volatile chemical in a sample of gas by the insects; and
    a power source wherein the width of said first channel and said second channel is approximately the width of said predetermined arrangement of the insects in said chamber and wherein the flow of said sample of gas is common to each of the insects due to said first channel being undivided.

19. The apparatus of claim 18, wherein said metal strip or mesh of the pre-concentrating means is separated from said holder by a spacer.

20. The apparatus of claim 18, wherein said metal strip or mesh is made of stainless steel.

* * * * *